US006638228B1

(12) United States Patent
Brock-Fisher et al.

(10) Patent No.: US 6,638,228 B1
(45) Date of Patent: Oct. 28, 2003

(54) CONTRAST-AGENT ENHANCED COLOR-FLOW IMAGING

(75) Inventors: George A. Brock-Fisher, Andover, MA (US); Jodi L. T. Perry, Methuen, MA (US); Patrick G. Rafter, Windham, NH (US); Mckee Dunn Poland, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/134,164

(22) Filed: Apr. 26, 2002

(51) Int. Cl.[7] .................................................. A61B 8/80
(52) U.S. Cl. ...................................................... 600/443
(58) Field of Search ................................. 600/443, 447, 600/455, 454, 448, 449, 437

(56) References Cited

U.S. PATENT DOCUMENTS

| 5,410,516 A | 4/1995 | Uhlendorf et al. ............. 367/7 |
| 5,566,674 A | * 10/1996 | Weng ........................ 600/443 |
| 5,577,505 A | 11/1996 | Brock-Fisher et al. . 128/662.02 |
| 5,860,931 A | * 1/1999 | Chandler .................... 600/458 |
| 6,224,557 B1 | * 5/2001 | Ziel et al. ................... 600/455 |
| 6,468,216 B1 | * 10/2002 | Powers et al. .............. 600/443 |

\* cited by examiner

Primary Examiner—Francis J. Jaworski
Assistant Examiner—Maulin Patel
(74) Attorney, Agent, or Firm—John Vodopia

(57) ABSTRACT

Systems and methods for enhanced color-flow imaging of contrast-agent perfused blood vessels and other tissues within a patient's body are disclosed. The method generally comprises, introducing one or more contrast agents into the body, power-modulating transmit pulses into the body, receiving echoes from the body, processing the received echoes to reduce tissue-generated echoes and echoes from stationary contrast agent, using a color-flow processor to generate a color-encoded display responsive to contrast-agent motion. The method may be implemented by a system with a an excitation-signal source, a transducer, an ultrasound-processing system having multiple image processors including a color-flow processor, as well as, a clutter filter, and an arbiter, and a display-processing system.

24 Claims, 10 Drawing Sheets

CONTRAST-AGENT ENHANCED COLOR-FLOW IMAGING

FIELD OF THE INVENTION

The present disclosure relates to ultrasonic imaging. More particularly, a system and method for improved contrast-agent enhanced-diagnostic evaluations are disclosed.

BACKGROUND OF THE INVENTION

Ultrasonic imaging has quickly replaced conventional X-rays in many clinical applications because of its image quality, safety, and low cost. Ultrasonic images are typically formed through the use of phased or linear-array transducers which are capable of transmitting and receiving pressure waves directed into a medium such as the human body. These ultrasonic transducers may be further assembled into a housing, which may contain control electronics, the combination of which forms an ultrasonic probe. Ultrasonic probes are used along with an ultrasonic transceiver to transmit and receive pressure waves through the various tissues of the body. The various ultrasonic responses are then processed by an ultrasonic-imaging system to display the various structures and tissues of the body.

Some ultrasound-imaging systems can create two-dimensional B-mode images of tissue in which the brightness of a pixel is based on the intensity of the received ultrasonic echoes. In another common imaging modality, typically known as color-flow imaging, the flow of blood or movement of tissue is observed. Color-flow imaging modalities take advantage of the Doppler effect to color-encode image displays. In color-flow imaging, the frequency shift of backscattered ultrasound waves is used to measure the velocity of the backscatterers from tissues or blood. The frequency of sound waves reflecting from the inside of blood vessels, heart cavities, etc. is shifted in proportion to the velocity of the blood cells. The frequency of ultrasonic waves reflected from cells moving towards the transducer is positively shifted. Conversely, the frequency of ultrasonic reflections from cells moving away from the transducer is negatively shifted. The Doppler shift may be displayed using different colors to represent speed and direction of flow. To assist diagnosticians and operators, the color-flow image may be superimposed on the B-mode image.

Current color-flow imaging techniques have disadvantages in that it is difficult to obtain diagnostic quality images from patients that have a poor acoustic window (i.e., patients having a relatively large volume of tissue between their skin and their rib cage for heart related studies). In addition, it is often difficult to separate desired blood-velocity signals from artifacts that result from moving tissue. This problem is most severe when there is not a relatively large difference in velocity between the tissue and the blood contained therein.

Ultrasonic imaging can be particularly effective when used in conjunction with contrast agents. In contrast-agent imaging, gas filled micro-sphere contrast agents known as microbubbles are typically injected into a medium, normally the bloodstream. Due to their physical characteristics, contrast agents stand out in ultrasound examinations and therefore can be used as markers that identify the amount of blood flowing to or through the observed tissue. In particular, the contrast agents resonate in the presence of ultrasonic fields producing radial oscillations that can be easily detected and imaged. Normally, this response is imaged at the second harmonic of the transmit frequency, $f_o$. By observing anatomical structures after introducing contrast agents, medical personnel can significantly enhance imaging capability for diagnosing the health of blood-filled tissues and blood-flow dynamics within a patient's circulatory system. For example, contrast-agent imaging is especially effective in detecting myocardial boundaries, assessing micro-vascular blood flow, and detecting myocardial perfusion.

U.S. Pat. No. 5,410,516 to Uhlendorf et al. discloses contrast-agent imaging along with single-pulse excitation techniques such as harmonic imaging. Specifically, Uhlendorf teaches that by choosing a radio frequency (RF) filter to selectively observe any integer harmonic (2nd, 3rd, etc.), subharmonic (e.g., ½ harmonic) or ultraharmonic (e.g., 3⁄2 harmonic) it is possible to improve the microbubble to tissue ratio. The second harmonic has proven most useful due to the large bubble response at this frequency as compared to higher-order integer harmonics, subharmonics or ultraharmonics. The second harmonic also is most practical due to bandwidth limitations on the transducer (i.e., <70% bandwidth, where percent bandwidth is defined as the difference of the high comer frequency –6 dB point from the low comer frequency –6 dB point, divided by the center frequency.) However, single-pulse excitation techniques together with harmonic imaging suffer from poor microbubble-to-tissue ratios as large tissue generated integer-harmonic signals mask the signals generated by the contrast agent.

As a result, of the discrimination problem associated with single-pulse excitation techniques, many multiple-pulse methodologies have been developed to suppress ultrasonic responses from anatomical tissues. These multiple-pulse excitation techniques result in diagnostic displays having an intensity that is responsive to the concentration of the contrast agent within the local insonified region.

Recently, it has been determined that tissue also produces harmonic responses which influence the images produced during contrast imaging. Several techniques have been developed which take advantage of the primarily linear response behavior of tissue to cancel or attenuate the linear-tissue signals. In several of these techniques, multiple-transmit lines are fired along the same line of sight into the body. The transmit waveform is modified (e.g., in terms of power, phase, or polarity) from line-to-line to produce a variation in the response received by the transducer. These data points are then processed to remove the influence of their linear components to yield data that primarily contains the non-linear response of the contrast agents.

Although the above-described techniques work well in removing the influence of stationary tissue, flash artifacts from moving tissue can degrade the resultant images. In particular, this movement causes decorrelation of the received echoes that is not compensated by typical processing techniques. This degradation can be substantial, particularly where the heart is being imaged due to its frequent and rapid motions. Attempts have been made to reduce the effects of such movement by applying two-zero filters to the responses of the receive signals associated with the various transmit lines. However, this technique assumes perfectly linear tissue movement and therefore is not completely effective in removing the moving tissue signals.

From the above, it can be appreciated that it would be desirable to have a method for contrast imaging in which the response of moving tissue is effectively suppressed so as to enhance the imaging sensitivity of the contrast agents. It will be further appreciated that it would be desirable to have a method for contrast imaging in which the response of moving tissue is effectively suppressed to permit quantitative assessment of flow velocities.

SUMMARY OF THE INVENTION

The present disclosure relates to apparatus and methods for imaging contrast agents within a patient's body. More specifically, the disclosure relates to a system and method that improves contrast-agent enhanced-diagnostic evaluations by applying a color-flow processing algorithm to ultrasonic-response data generated and processed by a power-modulation technique selected for the ability to suppress tissue signals. The method generally comprises introducing one or more contrast agents into the body, transmitting power-modulated ultrasonic pulses into the body, receiving echoed signals from the body, processing the received data (in the received echo signals) to suppress tissue-response signals, processing the received contrast-agent signals with a color-flow algorithm, examining the color-flow processed contrast-agent signals over time to generate a contrast-agent velocity estimate, and generating a color-encoded display of contrast-agent velocities.

In one embodiment, the ultrasound signal comprises a plurality of signal lines that have been modulated to have different transmit characteristics. The step of processing the received data to suppress tissue-motion generated response signals comprises repetitively applying a weighted finite-impulse-response (FIR) filter to slow-time samples to substantially remove tissue signals and applying the received sequence to a one-zero clutter filter. This has the effect of removing signals from stationary contrast-agent bubbles, while passing signals generated by moving contrast-agent bubbles.

In an alternative embodiment, the velocity of the moving tissue is measured to generate a secondary velocity signal. This secondary velocity signal is then mathematically combined with the velocity estimate from the power-modulated flow signal, producing a corrected measurement of the blood-flow velocity relative to the surrounding tissue, rather than relative to the ultrasonic probe (e.g., the transducer).

Briefly described, in architecture, the system can be implemented with an excitation signal source, a transducer, an ultrasound-processing system having multiple-image processors including a color-flow processor, as well as, a clutter-filter, and an arbiter, and a display-processing system.

Other features and advantages of the system and method for contrast-agent enhanced color-flow imaging will become apparent to one skilled in the art upon examination of the following drawings and detailed description. It is intended that all such additional features and advantages be included herein as protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

The present disclosure generally relates to contrast imaging. According to one aspect of the invention, a contrast-agent detection technique is used together with a tissue-signal suppression technique to image contrast-agent concentrations within blood vessels of contrast-agent perfused tissue. In another aspect of the invention, a tissue-motion velocity signal is isolated and used to correct blood-flow velocity information relative to the tissue rather than relative to the transducer. In either case, a color-flow processor is used together with a clutter filter to generate a signal representing contrast-agent velocities. The combination of the tissue-suppression feature of power modulation with flow-estimation feature of color-flow processing makes it possible to differentiate relatively slow-moving blood from moving tissue. Some exemplar clinical applications may include coronary-artery imaging, coronary-flow reserve assessment, blood-perfusion imaging, and tumor detection by imaging blood supply.

Figure 1:
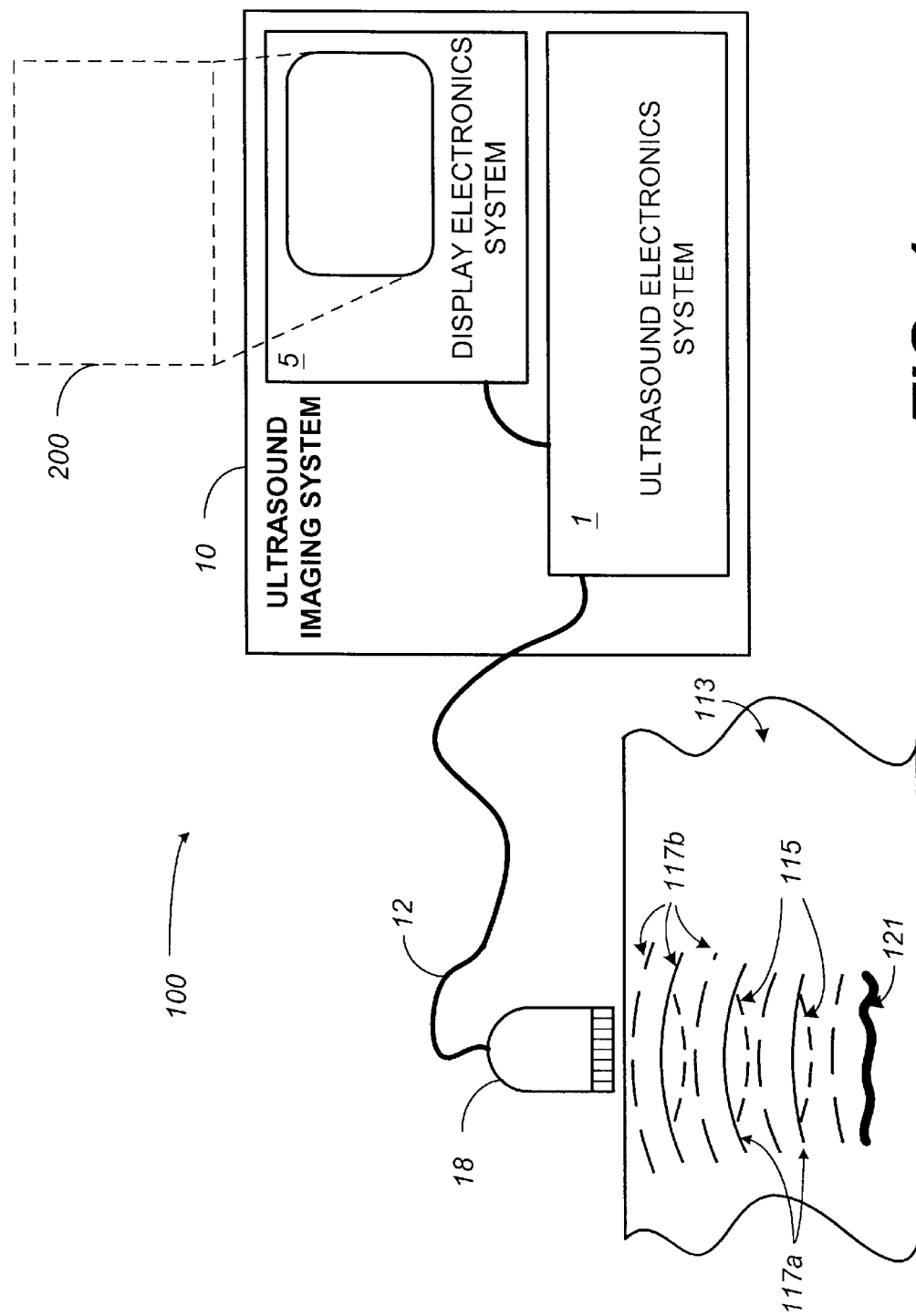
FIG. 1 is a schematic diagram of an exemplar diagnostic-imaging environment suited to the improved ultrasound-imaging system.

Referring now in more detail to the drawings, in which like numerals indicate corresponding parts throughout the several views, attention is now directed to FIG. 1, which illustrates the general diagnostic environment where an improved ultrasound-imaging system may practice the various methods enclosed herein to improve color-flow ultrasound-imaging diagnostics. In this regard, the a general diagnostic environment where the improved ultrasound-imaging system may practice the various methods of improved color-flow imaging is illustrated by way of a schematic diagram in FIG. 1 and is generally denoted by reference numeral 100. As illustrated in FIG. 1, an ultrasound-imaging system 10 may be disposed in a diagnostic environment 100 comprising a patient under test 113, a transducer 18, and an interface cable 12.

As illustrated in FIG. 1, the transducer 18 may be placed into position over a portion of the anatomy of a patient under test 113 by a user/operator (not shown) of the ultrasound-imaging system 10. As shown in FIG. 1, a plurality of transmit signals may be generated within the ultrasound-electronics system 1 and conveyed to the transducer 18 via the interface cable 12. The plurality of transmit signals may be converted to a plurality of transmit pulses 115 that emanate from the transducer 18 in response to the applied transmit signals.

When the transmit pulses (ultrasound energy) 115 encounter a tissue layer of the patient under test 113 that is receptive to ultrasound insonification, the multiple transmit pulses 115 penetrate the tissue layer 13. As long as the magnitude of the multiple ultrasound pulses exceeds the attenuation affects of the tissue layer 113, the multiple ultrasound pulses 115 will reach an internal target 121. Those skilled in the art will appreciate that tissue boundaries or intersections between tissues with different ultrasonic impedances will develop ultrasonic responses at the fundamental-transmit frequency of the plurality of ultrasound pulses 115. Tissue insonified with ultrasonic pulses will develop fundamental-ultrasonic responses that may be distinguished in time from the transmit pulses to convey information from the various tissue boundaries within a patient.

Those ultrasonic reflections 117a, 117b of a magnitude that exceed that of the attenuation affects from traversing tissue layer 113 may be monitored and converted into an electrical signal by the ultrasound-electronics system 1. As further illustrated in the diagram of FIG. 1, the ultrasound-electronics system 1 and a display-electronics system 5 may work together to produce an ultrasound-display image 200 derived from the plurality of ultrasonic echoes 117.

Those skilled in the art will appreciate that those tissue boundaries or intersections between tissues with different ultrasonic impedances will develop ultrasonic responses at both the fundamental frequency, as well as at harmonics of the fundamental frequency of the plurality of ultrasound pulses 115. Tissue insonified with ultrasonic pulses 115 will develop both fundamental 117a and harmonic ultrasonic responses 117b that may be distinguished in time from the transmit pulses 115 to convey information from the various tissue boundaries within a patient. It will be further appreciated that tissue insonified with ultrasonic pulses 115 develops harmonic responses 117b because the compressional portion of the insonified waveforms travels faster than the rarefactional portions. The different rates of travel of the compressional and the rarefactional portions of the waveform causes the wave to distort producing a harmonic signal, which is reflected or scattered back through the various tissue boundaries.

In some embodiments, the ultrasound-imaging system 10 both transmits and receives a plurality of ultrasound pulses 115 at a fundamental frequency. Those skilled in the art will appreciate that harmonic responses 117b may be received by a transducer 18 having an appropriately wide bandwidth to simultaneously transmit at a fundamental frequency and receive associated responses at a harmonic frequency thereof. While fundamental imaging is used, both fundamental and harmonic imaging are contemplated and within the scope of the present invention.

As further illustrated in FIG. 1, ultrasonic echoes 117a and 117b reflect fundamental responses and harmonic responses respectively. It is significant to note that while FIG. 1 illustrates a second harmonic response to the incident multiple ultrasound-transmit pulses 115 impinging the internal target 121 other harmonic responses may also observed. As by way of example, it is known that subharmonic, harmonic, and ultraharmonic responses may be created at the tissue boundary between a tissue layer 113 and the internal target 121, when the internal target has been perfused with one or more contrast agents. The internal target 121 alone will produce harmonic responses at integer multiples of the fundamental frequency. Various contrast agents on the other hand, have been shown to produce subharmonic, harmonic, and ultraharmonic responses to incident ultrasonic pulses. Those ultrasonic reflections of a magnitude that exceed that of the attenuation affects from traversing tissue layer 113 (e.g., fundamental, subharmonic, harmonic, and ultraharmonic responses) may be monitored and converted into an electrical signal by the combination of the transducer 18, the interface cable 12, and the ultrasound-electronics system 1 as will be explained in further detail below.

System Architecture and Operation

The architecture of an ultrasound-imaging system 10 capable of practicing the various contrast-agent imaging methods disclosed below is illustrated by way of a functional-block diagram in FIG. 2 and is generally denoted by reference numeral 10. Note that many of the functional blocks illustrated in FIG. 2 define a logical function that can be implemented in hardware, software, or a combination thereof. For purposes of achieving high speed, it is preferred, at present, that most of the blocks be implemented in hardware, unless specifically noted hereafter. It will be appreciated that this figure does not necessarily illustrate every component of the system, emphasis instead being placed upon the components relevant to the methods disclosed herein.

Figure 2:
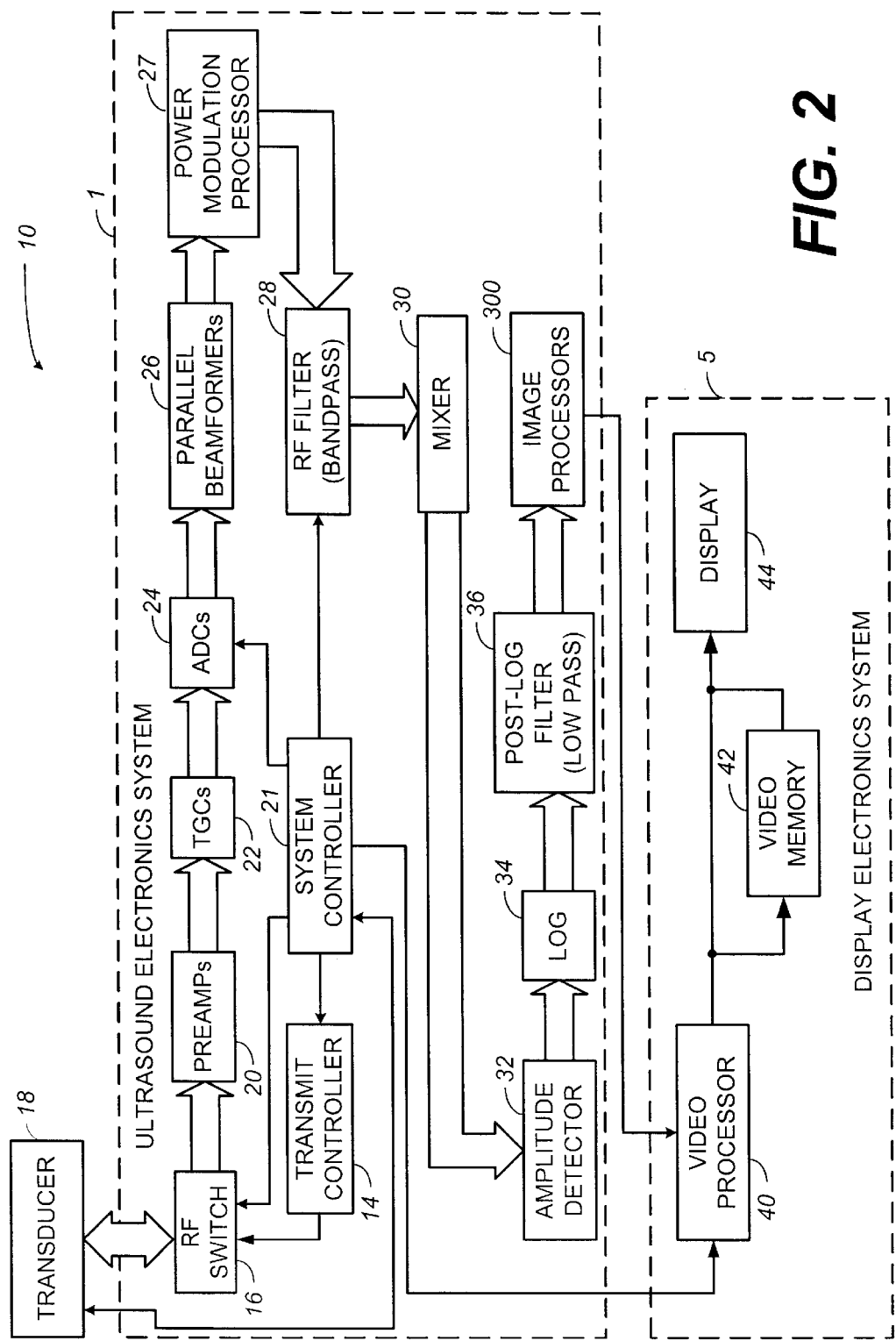
FIG. 2 is a functional-block diagram of an embodiment of the improved ultrasound-imaging system of FIG. 1.

Referring to FIG. 2, the ultrasound-imaging system 10 may include an ultrasound-electronics system 1 in communication with a transducer 18 and display-electronics system 5. As illustrated in FIG. 2, the ultrasound-electronics system 1 may include a system controller 21 designed to control the operation and timing of the various elements and signal flow within the ultrasound-imaging, system 10 pursuant to suitable software. The ultrasound-electronics system 1 may further comprise a transmit controller 14, a radio-frequency (RF) switch 16, a plurality of preamps 20, time-gain compensators (TGCs) 22, and analog-to-digital converters (ADCs) 24. In addition, the ultrasound-electronics system 1 may comprise a parallel beamformer 26, a power-modulation processor 27, a RF filter 28, a mixer 30, an amplitude detector 32, a log mechanism 34, a post-log filter 36, and one or more image processors 300. As further illustrated in FIG. 2, the display-electronics system 5 may comprise a video processor 40, a video-memory device 42, and a display 44.

The transducer 18 may take the form of a phased-array transducer having a plurality of elements both in the lateral and elevation directions. The plurality of transducer elements may be constructed of a piezoelectric material, for example but not limited to, lead-zirconate-titanate (PZT). Each element may be selectively supplied with an electrical pulse or other suitable electrical waveform, causing the elements to collectively propagate an ultrasound-pressure wave into the object-under-test. Moreover, in response thereto, one or more echoes are reflected by the object-under-test and are received by the transducer 18, which transforms the echoes into an electrical signal for detection and processing within the ultrasound-electronics system The array of elements associated with the transducer 18 enable a beam, emanating from the transducer array, to be steered (during transmit and receive modes) through the object by delaying the electrical pulses supplied to the separate elements. When a transmit mode is active, an analog waveform is communicated to each transducer element, thereby causing a pulse to be selectively propagated in a particular direction, like a beam, through the object.

When a receive mode is active, a waveform is sensed or received at each transducer element at each beam position. Each analog waveform essentially represents a succession of echoes received by the transducer element over a period of time as echoes are received along the single beam through the object. Time delays are applied to the signals from each element to form a narrow receive beam in the desired direction. The entire set of analog waveforms formed by both transmit and receive mode manipulations represents an acoustic line, and the entire set of acoustic lines represents a single view, or image, of an object commonly referred to as a frame.

As is known, a phased-array transducer may comprise a host of internal-electronics responsive to one or more control signals that may originate within the system controller 21 or alternatively in the transmit controller 14. For example, the transducer electronics may be configured to select a first subset of transducer elements to apply an excitation signal to generate a plurality of ultrasonic pulses. In a related manner, the transducer electronics may be configured to select a second subset of transducer elements to receive ultrasonic echoes related to the transmitted-ultrasonic pulses. Each of the aforementioned transducer-element selections may be made by the transducer 18 in response to the one or more control signals originating in the transmit controller 14 or the system controller 21.

As illustrated in FIG. 2, the transmit controller 14 may be electrically connected to the transducer 18 via a RF switch 16. The transmit controller 14 may be in further communication with the system controller 21. The system controller 21 may be configured to send one or more control signals to direct operation of the transmit controller 14. In response, the transmit controller 14 may generate a series of electrical pulses that may be periodically communicated to a portion of the array of elements of the transducer 18 via the RF switch 16, causing the transducer elements to emit ultrasound signals into the object-under-test of the nature described previously. The transmit controller 14 typically provides separation between the pulsed transmissions to enable the transducer 18 to receive echoes from the object during the period between transmit pulses and forwards them onto a set of parallel analog preamplifiers 20, herein labeled, "PREAMPs." The RF switch 16 may be configured to direct the various transmit and receive electrical signals to and from the transducer 18.

The plurality of preamplifiers 20 may receive a series of analog electrical-echo waveforms from the transducer 18 that are generated by echoes reflected from the object-under-test. More specifically, each preamplifier 20 receives an analog electrical-echo waveform from a corresponding set of transducer elements for each acoustic line. Moreover, the set of preamplifiers 20 receives a series of waveform sets, one set for each separate acoustic line, in succession over time and may process the waveforms in a pipeline-processing manner. The set of preamplifiers 20 may be configured to amplify the echo waveforms to provide amplified-echo waveforms to enable further signal processing, as described hereafter. Because the ultrasound signals received by the transducer 18 are of low power, the set of preamplifiers 20 should be of sufficient quality that excessive noise is not generated in the process.

Because the echo waveforms typically decay in amplitude as they are received from progressively deeper depths in the object-under-test, the plurality of analog preamplifiers 20 in the ultrasound-electronics system 1 may be connected respectively to a parallel plurality of TGCs 22, which are known in the art and are designed to progressively increase the gain during each acoustic line, thereby reducing the dynamic range requirements on subsequent processing stages. Moreover, the set of TGCs 22 may receive a series of waveform sets, one set for each separate acoustic line, in succession over time and may process the waveforms in a pipeline-processing manner.

A plurality of parallel analog-to-digital converters (ADCs) 24 may be in communication respectively with the plurality of TGCs 22, as shown in FIG. 2. Each of the ADCs 24 may be configured to convert its respective analog-echo waveform into a digital-echo waveform comprising a number of discrete-location points (hundreds to thousands; corresponding with depth and may be a function of ultrasound transmit frequency or time) with respective quantized instantaneous-signal levels, as is well known in the art. In prior art ultrasound-imaging systems, this conversion often occurred later in the signal processing steps, but now, many of the logical functions that are performed on the ultrasonic signals can be digital, and hence, the conversion is preferred at an early stage in the signal-processing process. Similar to the TGCs 22, the plurality of ADCs 24 may receive a series of waveforms for separate acoustic lines in succession over time and process the data in a pipeline-processing manner. As an example, the system may process signals at a clock rate of 40 MHz with a B-mode frame rate of 60 Hz.

A set of parallel beamformers 26 may be in communication with the plurality of ADCs 24 and may be designed to receive the multiple digital-echo waveforms (corresponding with each set of transducer elements) from the ADCs 24 and combine them to form a single acoustic line. To accomplish this task, each parallel beamformer 26 may delay the separate echo waveforms by different amounts of time and then may add the delayed waveforms together, to create a composite digital RF-acoustic line. The foregoing delay and sum beamforming process is well known in the art. Furthermore, the parallel beamformer 26 may receive a series of data collections for separate acoustic lines in succession over time and process the data in a pipeline-processing manner.

A power-modulation processor 27 may be coupled to the output of the parallel beamformers 26 and may be configured to receive and process a plurality of digital-acoustic lines in succession. The power-modulation processor 27 may be configured to work in concert with the system controller 21 or the transmit controller 14 to selectively process a plurality of digital-acoustic lines with multiple levels of ultrasound insonification. An example of an ultrasound-imaging system 100 for producing a series of ultrasonic pulses with multiple excitation levels is disclosed in U.S. Pat. No. 5,577,505 which shares a common assignee with the present application and the contents of which are incorporated herein in their entirety.

A RF filter 28 may be coupled to the output of the power-modulation processor 27 as illustrated in FIG. 2. The RF filter 28 may take the form of a bandpass filter configured to receive each digital-acoustic line and to remove undesired out of band noise. As further illustrated in FIG. 2, a mixer 30 may be coupled at the output of the RF filter 28. The mixer 30 may be designed to process a plurality of digital-acoustic lines in a pipeline manner. The mixer 30 may be configured to combine the filtered digital-acoustic lines from the RF filter 28 with a local oscillator signal (not shown for simplicity) to ultimately produce a plurality of baseband digital-acoustic lines.

Preferably, the local oscillator signal is a complex signal, having an in-phase signal (real) and a quadrature-phase signal (imaginary) that are ninety degrees out-of-phase. The mixing operation may produce sum and difference frequency signals. The sum-frequency signal may be filtered (removed), leaving the difference-frequency signal, which is a complex signal at near zero frequency. A complex signal is desired to follow direction of movement of anatomical structures imaged in the object-under-test, and to allow accurate, wide-bandwidth amplitude detection.

Up to this point in the ultrasound-echo receive process, all operations can be considered substantially linear, so that the order of operations may be rearranged while maintaining substantially equivalent function. For example, in some systems it may be desirable to mix to a lower intermediate frequency (IF) or to baseband before beamforming or filtering. Such rearrangements of substantially linear-processing functions are considered to be within the scope of this invention.

An amplitude detector 32 may receive and process, in pipeline manner, the complex baseband digital-acoustic lines from the mixer 30. For each complex-baseband digital-acoustic line, the amplitude detector 32 may analyze the envelope of the line to determine the signal intensity at each point along the acoustic line to produce an amplitude-detected digital-acoustic line. Mathematically, this means that the amplitude detector 32 determines the magnitude of each phasor (distance to origin) corresponding with each point along the acoustic line.

A log mechanism 34 may receive the amplitude-detected digital-acoustic lines in a pipeline-processing manner, from the amplitude detector 32. The log mechanism 34 may be configured to compress the dynamic range of the data by computing the mathematical logarithm (log) of each acoustic line to produce a compressed digital-acoustic line for further processing. Implementation of a log function enables a more realistic view, ultimately on a display, of the change in brightness corresponding to the ratio of echo intensities.

A post-log filter 36, usually in the form of a low-pass filter, may be coupled to the output of the log mechanism 34 and may be configured to receive the compressed digital-acoustic lines in a pipeline fashion. The post-log filter 36 may remove or suppress high frequencies associated with the compressed digital-acoustic lines to enhance the quality of the display image. Generally, the post-log filter 36 softens the speckle in the displayed image. The low-pass post-log filter 36 can also be configured to perform anti-aliasing. The low-pass post-log filter 36 can be designed to essentially trade spatial resolution for gray-scale resolution.

One or more image processors 300 may be coupled to the output of the low-pass post-log filter 36. Each of the image processors 300 may further comprise a suitable species of random-access memory (RAM) and may be configured to receive the filtered digital-acoustic lines from the low-pass post-log filter 36. The acoustic lines can be defined within a two-dimensional coordinate space. The image processors 300 may be configured to mathematically manipulate image information within the received and filtered digital-acoustic lines. In addition, each of the image processors 300 may be configured to accumulate acoustic lines of data over time for signal manipulation. In this regard, the image processors 300 may further comprise a scan converter to convert the data as stored in the RAM to produce pixels for display. Each scan converter may process the data in the RAM once an entire data frame (i.e., a set of all acoustic lines in a single view, or image/picture to be displayed) has been accumulated by the RAM. For example, if the received data is stored in RAM using polar coordinates to define the relative location of the echo information, the scan converter may convert the polar-coordinate data into rectangular (orthogonal) data capable of raster scan via a raster-scan capable processor. The ultrasound-electronics system 1, having completed the receiving, echo recovery, and image-processing functions, to form a plurality of image frames associated with the plurality of ultrasound-image planes, may forward the echo-image data information associated with each image frame to a display-electronics system 5 as illustrated in FIG. 2.

The display-electronics system 5 may receive the echo-image data from the ultrasound-electronics system 1, where the echo-image data may be forwarded to a video processor 40. The video processor 40 may be designed to receive the echo-image data information and may be configured to raster scan the image information. The video processor 40 outputs picture elements (e.g., pixels) for storage in a video-memory device 42 and/or for display via a display 44. The video-memory device 42 may take the form of a digital-videodisc (DVD) player/recorder, a compact-disc (CD) player/recorder, a video-cassette recorder (VCR), or other video-information storage device. As is known in the art, the video-memory device 42 permits viewing and or post-data collection image processing by a user/operator in other than real-time.

A display device in the form of a display 44 may be in communication with both the video processor 40 and the video memory 42 as illustrated in FIG. 2. The display 44 may be configured to periodically receive the pixel data from either the video memory 42 and or the video processor 40 and drive a suitable screen or other imaging device (e.g., a printer/plotter) for viewing of the ultrasound image by a user/operator.

Contrast-Agent Imaging

As used herein, power level relates to insonification or acoustic intensity. Mechanical index is one parameter used to measure acoustic intensity. Mechanical index is a United States Food and Drug Administration (FDA) regulated parameter defined as peak-rarefactional pressure in mega-Pascal (Mpa) divided by the square root of the center frequency in megahertz (MHz). Current FDA regulations limit the mechanical index to a maximum of 1.9, after allowing for tissue related frequency dependent attenuation.

It is important to note that different contrast agents respond differently to various insonification and detection techniques. It is theorized that these different responses can be explained due to flexibility of the shell material used to encase the agent, the size distribution within the body, and the particular characteristics of the gas inside the shell. As a result, determining an effective-mechanical index for a particular application is somewhat patient and agent specific. The mechanical index needs to be low enough to not destroy the contrast agent while maintaining a linear response signal from insonified tissue. On the other hand, the mechanical index needs to be high enough to overcome the effects of tissue attenuation at the fundamental frequency while initiating a non-linear response from the one or more contrast agents. Generally, a mechanical index from 0.05 to 0.5 will meet these requirements for a broad range of contrast agents starting from the most fragile to the more resilient.

As described earlier with regard to FIGS. 1 and 2 achieving different power levels in each of two or more transmit events or ultrasound lines 115 (see FIG. 1) may be accomplished in several different ways. A method of achieving the different power settings is by varying the transmit voltage. Varying transmit voltage has the direct result of varying the pressure amplitude of the resultant transmitted-ultrasound lines 115 (see FIG. 1). Alternatively, different power levels may be accomplished by controlling the size of the aperture of the transducer 18. The aperture size may be varied in the lateral or elevation dimensions by using a synthetic-aperture methodology. The aperture may be divided into two or more groups with transmit-ultrasound lines 115 being separately fired from each group. The subsequent reflected energy is then stored. The entire aperture is then used to transmit a second incident pressure wave with an increased energy level. The subsequent reflected energy is again stored. In this embodiment, the scaling step includes beamforming the response from the two or more smaller apertures and subtracting those results from the response due to excitation from the entire aperture to determine the non-linear response.

Another way of controlling transmitted-power levels is to fire a subset of elements in the array and compare the scaled-subset response to a response from the entire transducer array. This method should be performed in a manner to reduce and or minimize grating lobes that stem from under sampling the aperture and steering errors that result from asymmetries about the center of the aperture.

A non-limiting example of a multi-pulse technique that fires three pulses is described below. Firing the "even" numbered elements within transducer 18 may generate the first pulse. The second pulse may be generated by controllably firing all elements of the transducer 18. Firing the "odd" numbered elements may generate the third pulse. The response signal-processing portion of the ultrasound-electronics system 10 may be configured to mathematically combine a response from the first and third pulses for further mathematical manipulation with the second response signal. It is important to note that the selection of elements to form the various element subsets for the first and third pulses is not limited to "even" and "odd" numbered elements of the transducer element array. It will be appreciated by those skilled in the art that more than three pulses may be generated and fired to further extend a multi-pulse insonification and imaging technique.

The multi-pulse technique described above serves a couple of purposes. First, adjusting the transmitted power by firing a subset of elements reduces the transmit power while providing the same voltage level to each transmission. If the transmit waveforms are not properly scaled and inverted, or if the waveforms differ in their frequency content, undesired residual artifacts from imperfect tissue-response signal cancellations may be introduced by the ultrasound-electronics system 10. By matching the voltage level used to generate the various pulses, the ultrasound-electronics system 10 reduces any undesired tissue signals introduced by mathematically combining signal responses generated from ultrasonic transmissions of varying power levels. Transmit-waveform power-magnitude matching over a number of various levels of comparison across a received bandwidth of interest will serve to reduce residual-tissue response-signal artifacts that may result from transmit-power mismatches.

A second important result from using the multi-pulse technique is that by mathematically combining the first pulse response with the third pulse response, motion of an organ-of-interest (i.e., the heart) is averaged, so that when the second pulse response is mathematically processed (i.e., subtracted) from the combination of the first and third pulse responses, motion is suppressed between the various pulses.

Yet another way of suppressing the linear response of tissues is to use a phase-inversion technique. Phase-inversion techniques are well understood by those skilled in the art of ultrasonic imaging. The description of an ultrasonic-imaging system capable of producing, detecting, and image-processing ultrasonic responses that use phase-inversion techniques need not be described to understand the present invention and need not be described herein. It is significant to note, however, that mathematical post-processing of detected-response signals may vary based on the desired effect of the processing and the phase of the transmitted waveforms responsible for the response signals. By coordinating one or more of the phase, intensity, and frequency content of multiple transmitted pulses with the applicable response processing, motion artifacts between pulses may be substantially reduced.

Another technique that may be used to vary the transmitted levels would be to take advantage of the beam shape of a pressure wave. Transmitted pressure waves have a reduced magnitude that varies with angular distance. As by way of a non-limiting example, if a pressure wave is transmitted at 0 degrees (from the face of the transducer-element array) and the ultrasound-electronics system 10 is configured to receive responses at 0.0 and at 0.25 degrees, the power received at 0.25 degrees will be lower since it is off the peak of the transmitted beam.

Figure 3:
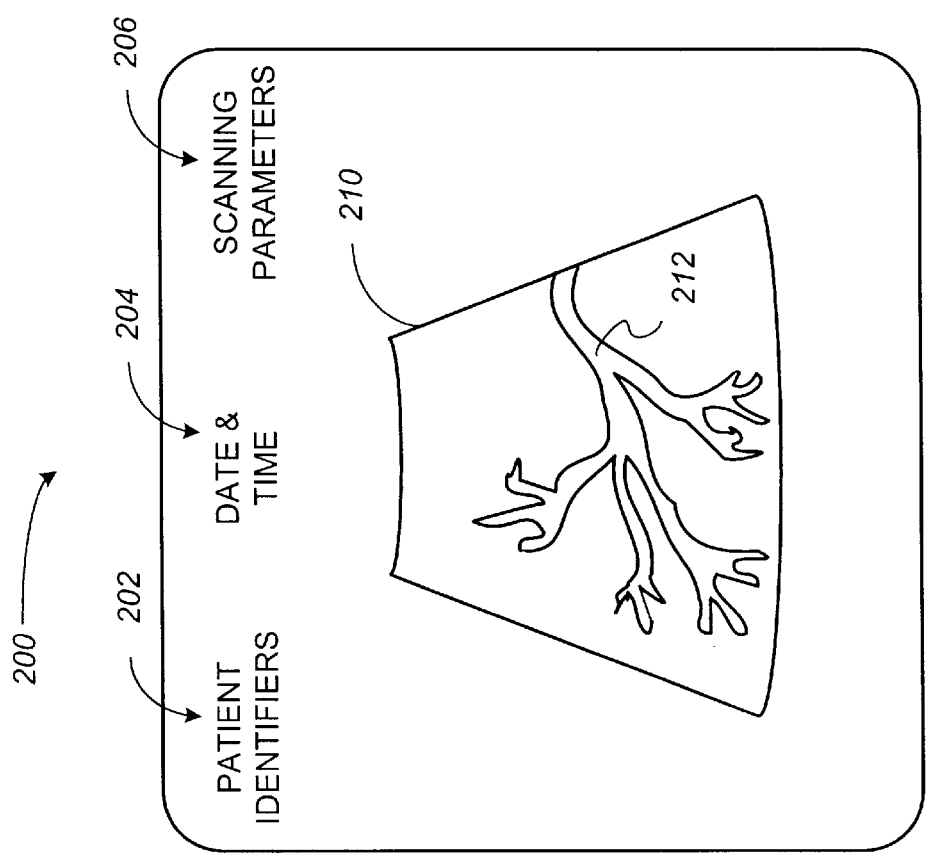
FIG. 3 is a schematic diagram of an exemplar diagnostic image that can be produced with the ultrasound-imaging system of FIG. 2.

An exemplar diagnostic-imaging environment 100 suited to the improved ultrasound-imaging system 10 having been described with regard to FIGS. 1 and 2, reference is now directed to FIG. 3, which illustrates a diagnostic image that can be produced with the improved ultrasound-imaging system 10 of FIG. 2. In this regard, ultrasound image 200 may comprise alphanumeric information in the form of patient identifiers 202, date and time identifiers 204 and scanning parameters 206. In addition to the one or more alphanumeric identifiers, ultrasound image 200 may comprise a real-time ultrasound image display 210 of structure in a body such as a portion of the circulatory system such as a coronary-blood vessel 212.

A clinical technician, to ascertain and locate an area of interest (e.g., a portion of the myocardium of a patient's heart muscle), may use a real-time image. Preferably the image is created from echoes returned from the non-destructive ultrasonic imaging of one or more contrast agents that have been introduced into the bloodstream of the patient. It is important to note that real-time contrast-agent images may be acquired at any phase of the heart cycle, not just when the heart is predominately at rest. While the aforementioned real-time imagery of the heart is especially useful in cardiology, variations of this method may prove useful in radiology where anatomical structures are more stationary as well.

Figure 4:
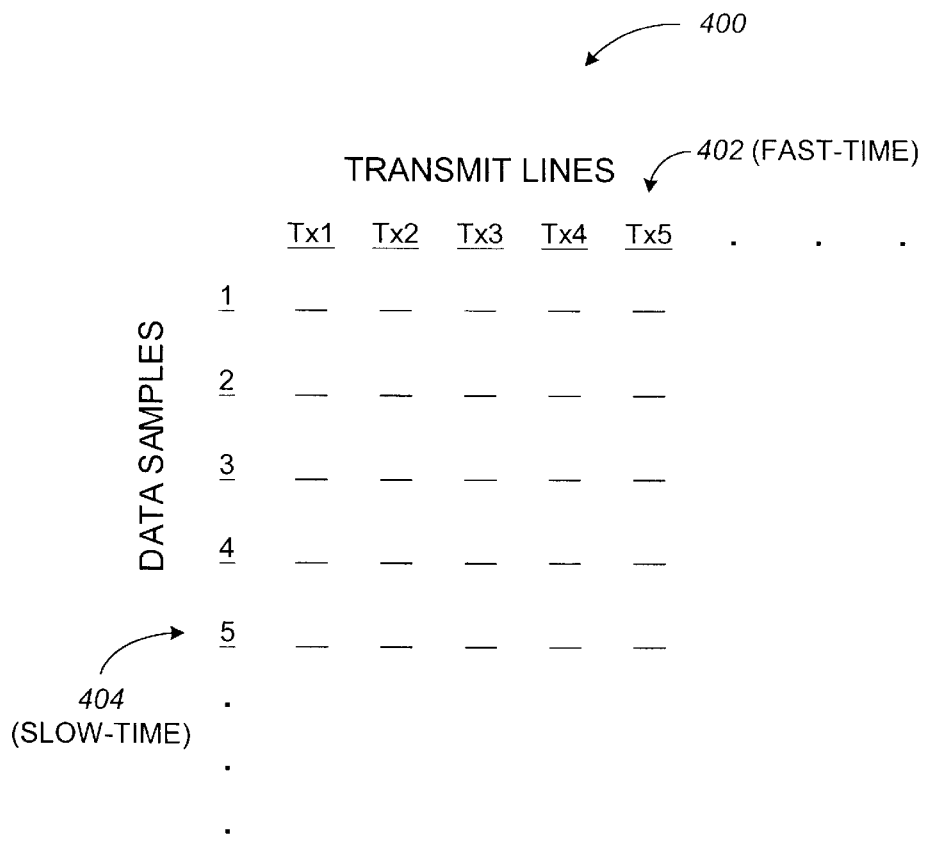
FIG. 4 is a schematic diagram illustrating power modulation as may be practiced by the ultrasound-imaging system of FIG. 2.

Irrespective of the particular transmit-signal modulation-technique used, each transmit line normally comprises repeated sequences of waveforms. By way of example, each waveform comprises a Gaussian-modified sinusoid. The various transmit lines are fired along the same line-of-sight into the body as indicated in FIG. 4. Each group of lines fired in this direction is referred to as a packet of lines. Normally, specific sequences of transmit waveforms are used and repeated multiple times within each packet. Each sequence of transmit waveforms is referred to as a sub-packet.

After the multiple lines have been transmitted into the body, the response echoes are received. Again, these received signals are digitized so that the data contained therein can be processed in the appropriate manner. Once digitized, these received data may be stored in one or more of the image processors 300 (FIG. 2). Preferably, the data are organized in an array of data points 400 as shown in FIG. 4.

The array 400 may comprise as many columns 402 as there are lines in the packet. Each column 402 contains a collection of samples which correlate to a particular transmit line. There are as many rows 404 in the array 400 as there are digitized-data samples along any one of the received lines. Each successive sample along a row 404 is representative of a particular imaging depth, but acquired a full line-time after the previous sample. Normally, the row 404 direction of the array 400 is referred to as slow-time. Each successive data point down each column 402 is acquired immediately after the previous data point in the line. Accordingly, the column direction of the array 400 is referred to as fast-time.

Once the various received data have been stored in the array 400, the first stage of processing can be conducted. First, a correction function is applied to the data to compensate for the variance of the transmit signals across the multiple transmit lines. The nature of the correction function may depend upon the particular modulation scheme used to vary the transmit signals. For instance, if the transmit signals were varied according to amplitude (i.e., power modulation), the correction function can comprise a scaling factor which accounts for the amplitude variance across the signal lines. If phase modulation was used in creating the transmit signals, the correction function can comprise a phase adjustment which accounts for the phase variance of the transmit signal. Similarly, where the transmit signals were varied in polarity, the correction can comprise inverting the receive data for the positive or the negative transmit lines.

After the transmit variance has been accounted for in the manner described above, the various lines of data can be subtracted from the other, for instance with a contrast-imaging clutter filter, to cancel the linear components of the data. However, before this cancellation is effected, the response of moving tissue is suppressed. As will be understood by persons having ordinary skill in the art, if there is any appreciable motion of tissue between the successive lines of the packets, the received-echo data will not cancel precisely, and some residual signal due from moving tissue will remain. Therefore, it is preferable to compensate for this motion before attempting to cancel the linear signals of moving tissue from the received data.

As also illustrated in FIG. 4, a power modulated multi-line subpacket having the following transmit sequence: 0, L, H, L, 0 may be applied by the ultrasound-electronics system 1 (FIG. 2). The initial blank line allows time for reverberation from a previous imaging line to die out. A FIR filter may then be applied to combine the slow-time samples 404 with weighted values: 0, -1, 1, -1, 1. This filtering results in the substantial reduction of tissue-generated signals and reverberation signals, while having little or no effect on signals from contrast-agent bubbles.

Figure 5:
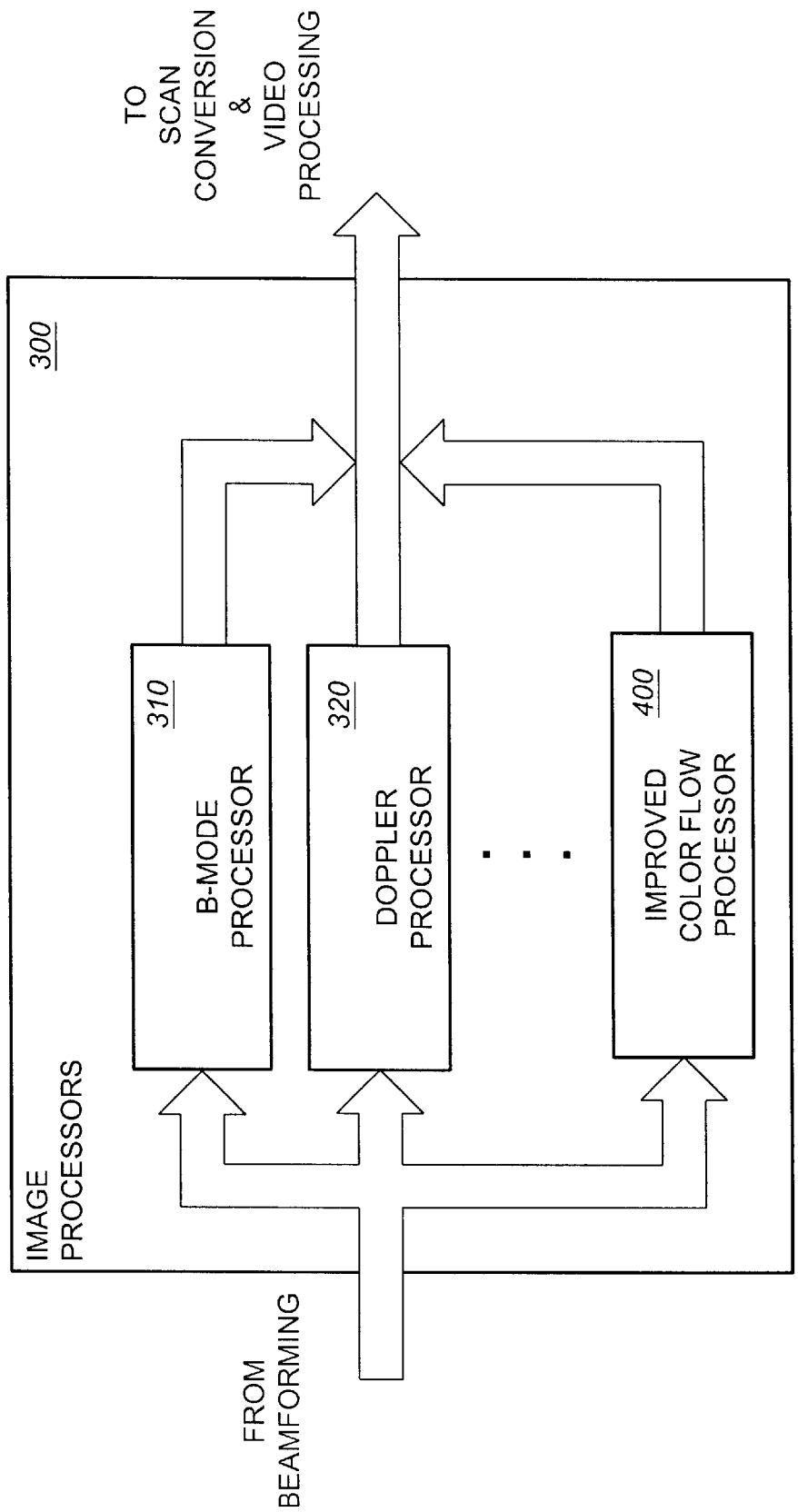
FIG. 5 is a functional-block diagram further illustrating a plurality of image processors within the ultrasound-imaging system of FIG. 2.

The data-point array 400 and the weighted FIR filtering of a multiple transmit line sequence having been described with regard to FIG. 4, reference is now directed to FIG. 5, which illustrates some of the image processors 300 that may be provided in the ultrasound-electronics system 10 of FIG. 2. In this regard, image processors 300 may comprise a B-mode processor 310, a Doppler processor 320, an improved color-flow processor 400, as well as other image processors. As shown in the functional-block diagram of FIG. 5, the image processors 300 may be inserted in the architecture of the ultrasound-electronics system 10 generally after beamforming (i.e., the parallel beamformers 26) and prior to scan conversion and video processing (i.e., in the display-electronics system 5). As previously described in association with FIG. 2, it will be appreciated that each of the image processors 300 may be configured with its own scan converter (not shown). It will be further appreciated that one or more scan converters may be provided in association with one or more of the various image processors 310, 320, 400.

Figure 6:
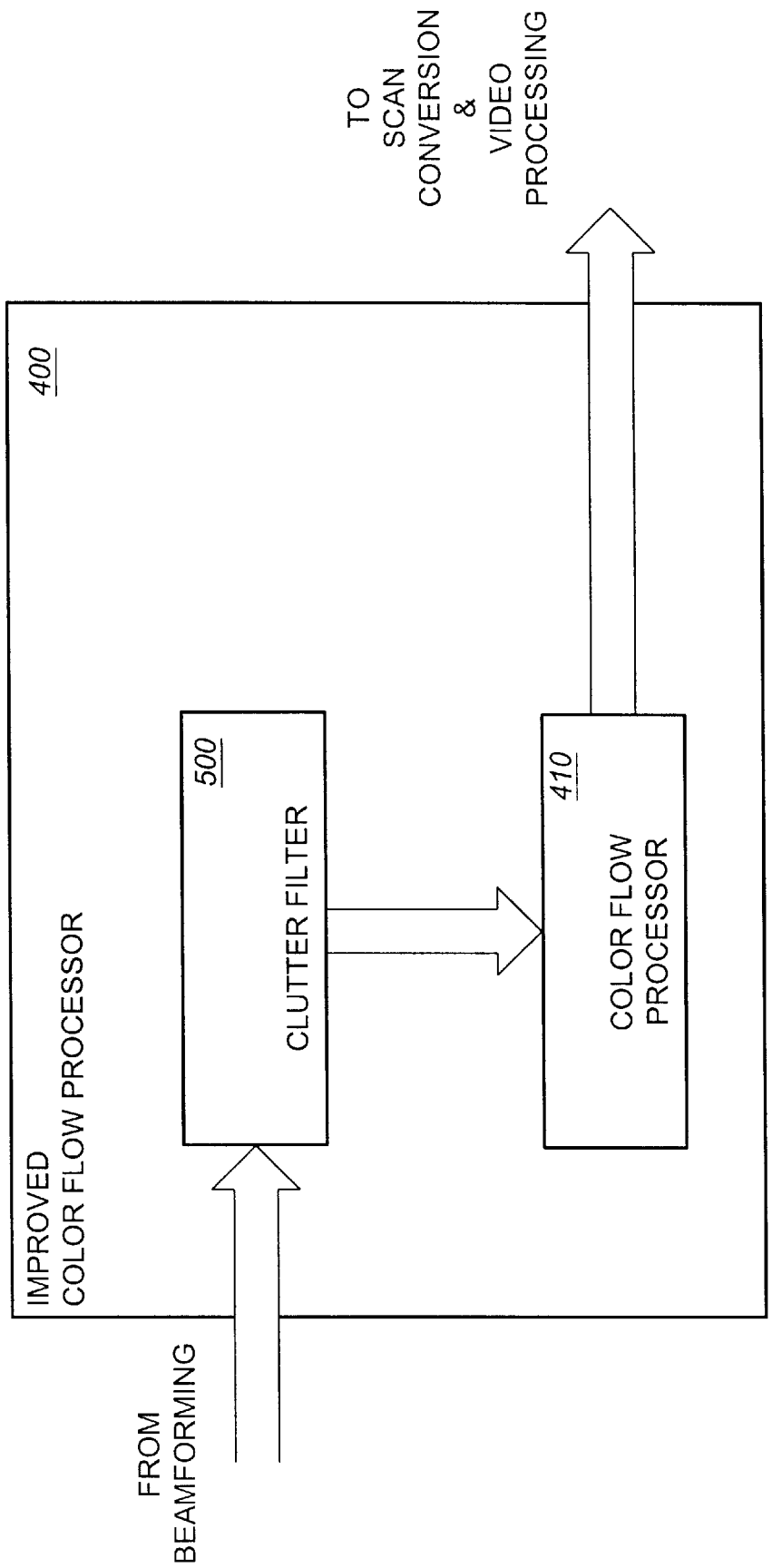
FIG. 6 is a functional-block diagram illustrating an embodiment of the improved color-flow processor introduced in FIG. 5.
Figure 7:
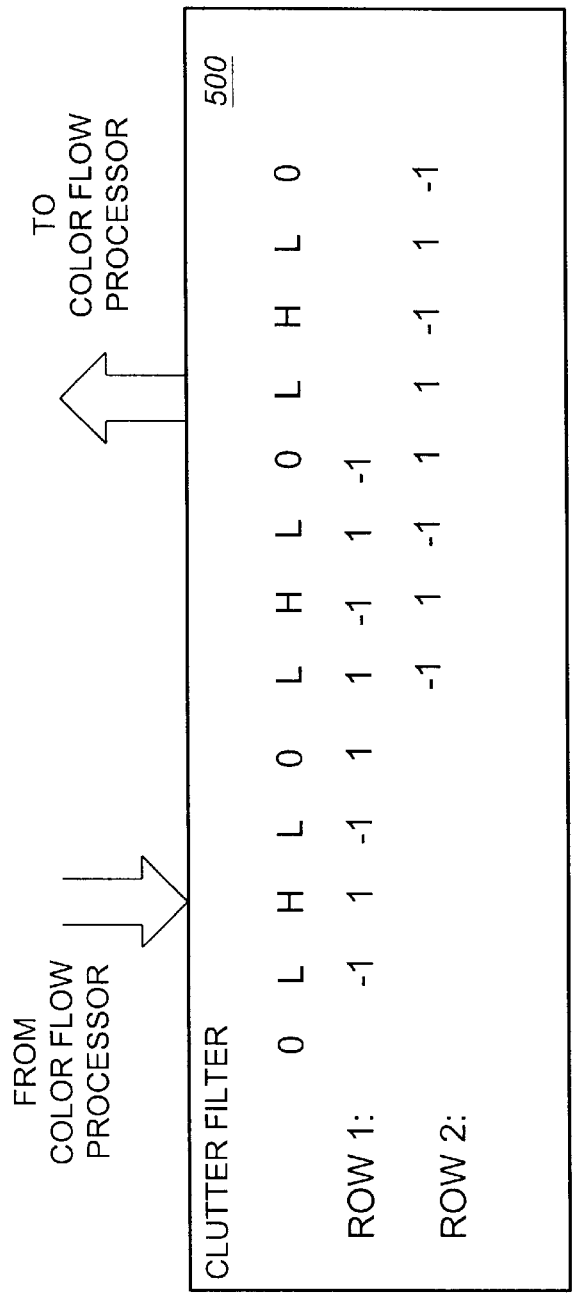
FIG. 7 is a schematic diagram illustrating operation of the clutter filter of FIG. 6.

An improved color-flow processor 400 is illustrated via a functional-block diagram in FIG. 6. In this regard, the improved color-flow processor 400 may comprise a clutter filter 500 in combination with a color-flow processor 410 known in the art. As shown in the previous illustration, the improved color-flow processor 400 may be introduced after parallel beamforming and prior to scan conversion. FIG. 7 further illustrates the operation of the clutter filter 500 introduced in FIG. 6.

In this regard, the power-modulation processor 27 of the ultrasound-electronics system 10 (see FIG. 2) may be configured to transmit the exemplar power-modulated transmit sequence illustrated across the top of FIG. 7. More specifically, the power-modulated transmit sequence may comprise the following 13 line packet: 0, L, H, L, 0, L, H, L, 0, L, H, L, 0. As shown in FIG. 7, 0 indicates no transmit pulse is sent; "L" indicates that a half-power transmit pulse is sent; and "H" indicates that a full-power transmit pulse is applied to the tissue of interest. In accordance with the improved color-flow processor 400, the clutter filter 500 for the exemplar 13 line transmit sequence may provide two output samples for color-flow processing with the weights as illustrated in FIG. 7. It can be seen that the clutter filter 500 applied to each sample is a one-zero filter (with a sample spacing of four slow-time samples). Convolved with the power-modulation FIR filter described above, the cumulative effect of the two filters and the power-modulation technique(s) is to reduce tissue generation signals and stationary contrast-bubble signals, while passing signals generated from moving contrast-agent bubbles.

In accordance with well known color-flow processing techniques, the relative phase of the two data points from the exemplar line sequence 13 of FIG. 7 can then be evaluated to compute a velocity estimate of the contrast-agent bubbles. The technique described above can also be applied to Doppler-imaging modes including phased-array pulsed-wave (PW) Doppler.

An advantage that results from the combination of the tissue-suppression feature of power modulation with the flow-estimation technique of color flow as applied to contrast-agent enriched blood, is it is now possible to differentiate slowly-moving blood flows (e.g., in the small blood vessels of the myocardium and vessels within organs other than the heart) from moving tissue. Furthermore, it is now possible to utilize contrast agents to enhance and improve the diagnostic quality of a color-flow exam on patients with poor acoustic windows.

Contrast-agent Enhanced Color Flow With Tissue Signal Velocity Adjustment

Figure 8:
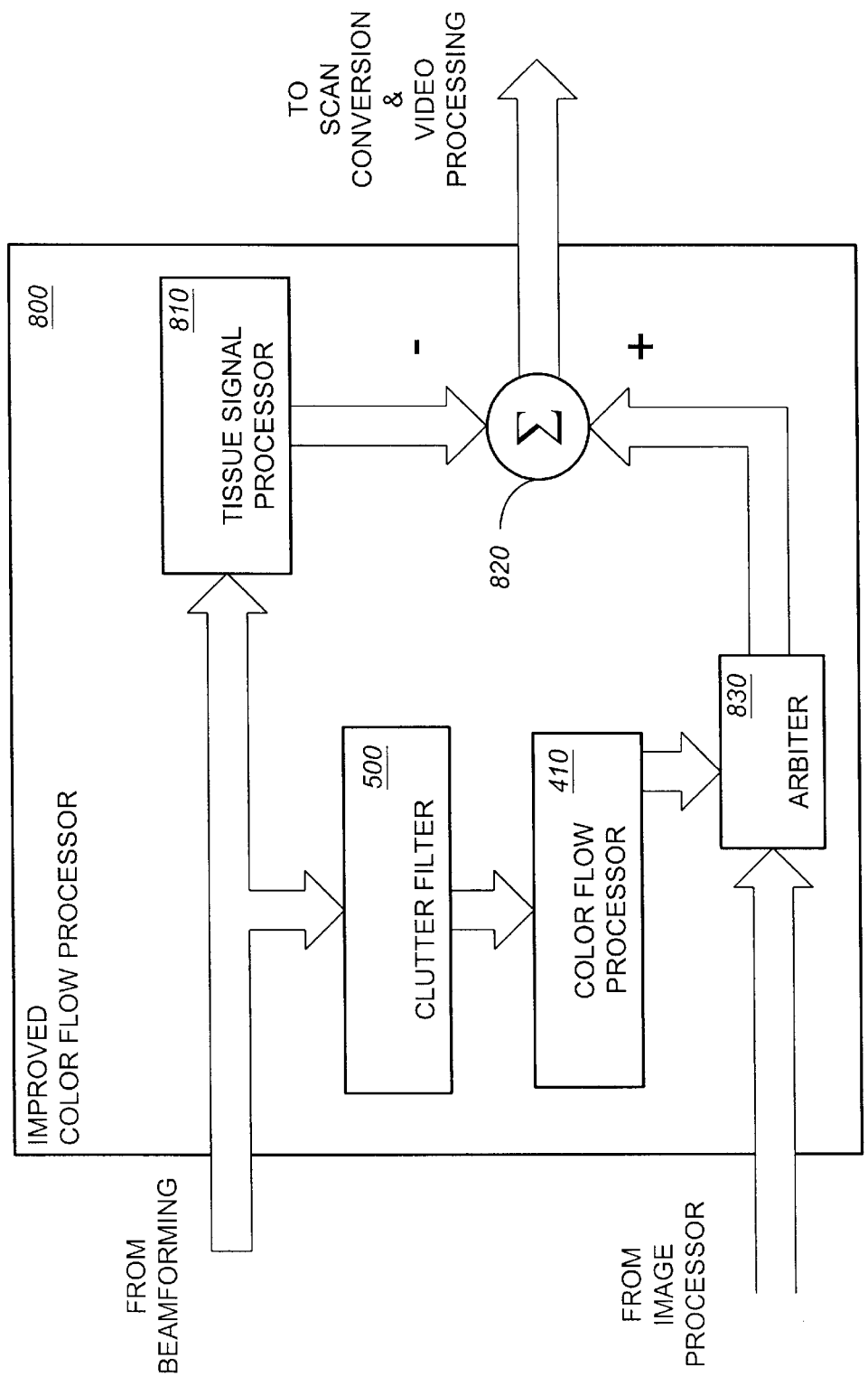
FIG. 8 is a functional-block diagram illustrating an alternative embodiment of the improved color-flow processor of FIG. 5.

Reference is now directed to FIG. 8, which illustrates a functional-block diagram of an alternative embodiment of an improved color-flow processor. As illustrated in FIG. 8, an improved color-flow processor 800 may comprise a clutter filter 500, a color-flow processor 410, a tissue-signal processor 810, a mathematical junction 820, and an arbiter 830. As previously described in association with FIG. 6, the improved color-flow processor 800 may also be inserted in the ultrasound-electronics system 10 of FIG. 2 generally after beamforming (i.e., the parallel beamformers 26) and prior to scan conversion and video processing (i.e., in the display-electronics system 5). As previously described in association with FIG. 2, it will be appreciated that the improved color-flow processor 800 may be configured with its own scan converter (not shown).

As illustrated in the functional-block diagram of FIG. 8, the improved color-flow processor 800 can be constructed by providing a secondary-processing path, not entirely separate from the path previously described with regard to the improved color-flow processor of FIG. 6. More specifically, the secondary-processing path may comprise a first branch that enters a tissue-signal processor 810 before being forwarded to the mathematical junction 820. A primary branch or color-flow-processing path may be formed by the clutter filter 500, the color-flow processor 410, and a signal from an image processor. The signal from the image processor and the output of the color-flow processor 410 are processed by the arbiter 830 before being forwarded to the mathematical junction 820. The secondary-processing path is designed to measure the velocity of the tissue generated echo signals rather than the blood with the contrast agent.

The tissue-generated echo signals can be applied to the tissue-signal processor 810 to generate a tissue-velocity signal formed from the same set of acoustic lines (i.e., the same subpacket data) as the power-modulated color-flow signal. However, the tissue-signal processor 810 will employ a different set of coefficients in its own clutter filter (not shown). The tissue-signal processor coefficients could, for example, select equal power lines from each subpacket, such as the "H" transmit lines and coefficients of 0 for the lower-power "L" transmit lines. The tissue-signal processor 810 would then produce the same output-sample rate as the clutter filter 500, and could be processed by the same phase-detection steps as the color-flow signal.

As illustrated in FIG. 8, and in accordance with standard color-flow processing techniques, the signal that exits the color-flow processor 410 (i.e., the color-flow velocity signal) is processed along with the underlying image data from a two-dimensional image processor (e.g., black and white image data as supplied by a B-mode processor). Where color-flow velocity samples are above a pre-defined (or user adjustable) intensity threshold, the color-flow velocity samples are rendered instead of the underlying image-data samples. In the improved color-flow processor 800, the arbitration between the color-flow velocity samples and the underlying image-data samples would remain unchanged, but where color-flow velocity samples are selected for display, the tissue-velocity signal would be subtracted. As a result, the improved color-flow processor 800 would provide a signal over time that suppresses the tissue "flash" artifact along with providing information regarding the velocity of contrast agents corrected for surrounding tissue motion.

Figure 9:
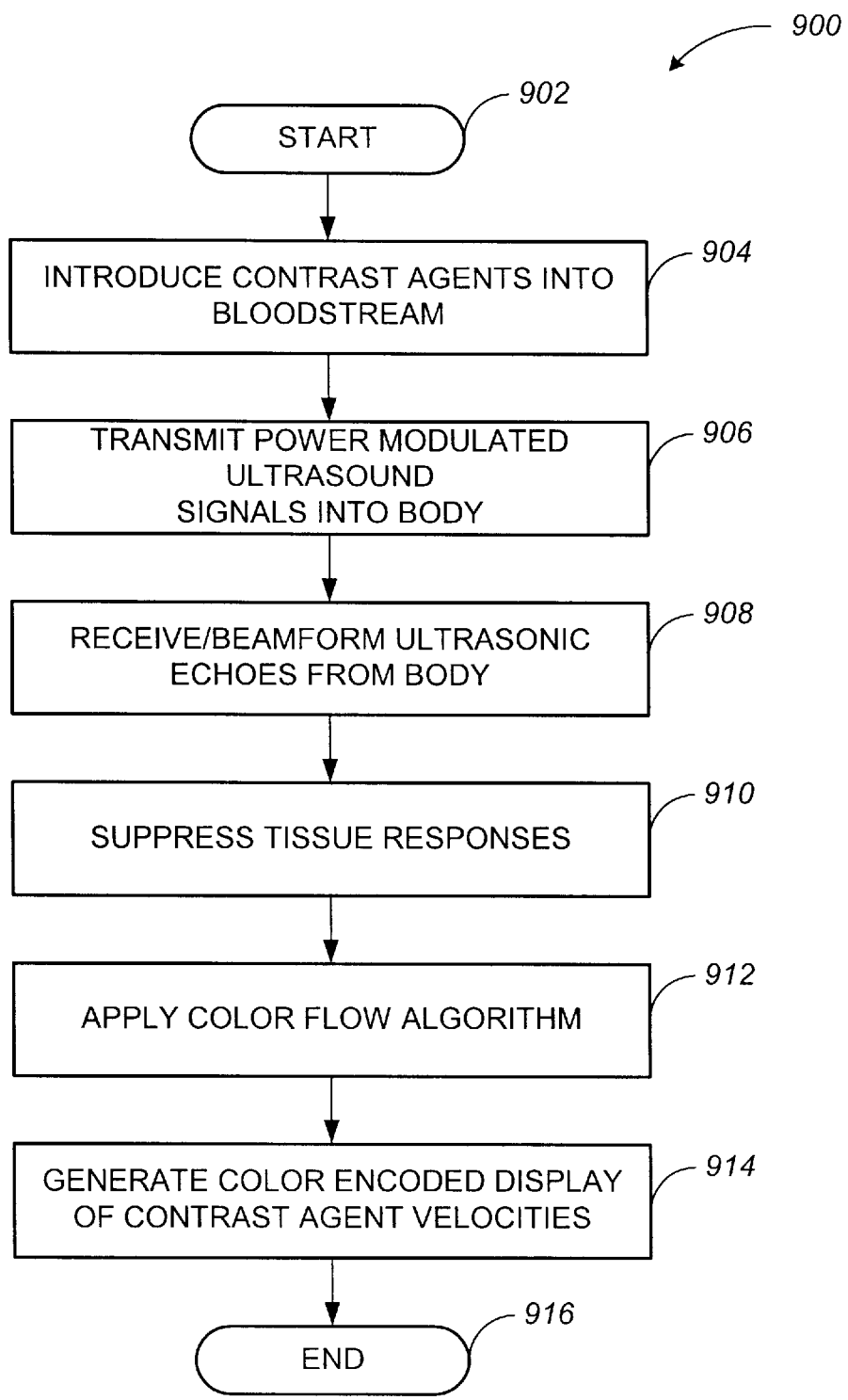
FIG. 9 is a flow chart illustrating a method for improved imaging of blood flow within moving tissue that may be practiced by the ultrasound-imaging system of FIG. 2.

Reference is now directed to FIG. 9, which illustrates a flowchart describing a method for contrast-agent enhanced color-flow imaging that may be implemented by the ultrasound-electronics system 10 of FIG. 2. As illustrated in FIG. 9, the method for contrast-agent enhanced color-flow imaging 900 may begin with step 902, labeled "START." First, one or more contrast agents may be introduced into a patient's bloodstream as indicated in step 904. These contrast agents can comprise microbubbles of a heavy gas, such as a perfluorocarbon-gas encapsulated in an outer shell made of protein, lipid, or other suitable material. Although the size of the agents may vary depending upon the application, these microbubbles normally are in the range of approximately 1.0 to 15 microns ($\mu$m) in diameter. As the contrast agents are introduced into the bloodstream, they travel throughout the cardiovascular system.

After having confirmed that tissues of interest (e.g., coronary blood vessels within the myocardium) contain sufficient amounts of the contrast agent(s), the ultrasound-electronics system 10 may be configured to transmit a series of power-modulated ultrasound signals into the body as shown in step 906.

As shown in step 908, the ultrasound-electronics system 10 is configured to receive the series of ultrasonic echoes induced by the power-modulated transmit signals. Next, as illustrated in step 910, non-linear tissue responses can be suppressed using power-modulation techniques as previously described hereinabove. After the effects of the moving-tissue signals have been suppressed, the various data can be processed using a color-flow-processing algorithm as shown in step 912. It is significant to note that the color-flow-processing will include processing by the clutter filter 500 to reduce the effect of echo signals generated by stationary contrast-agent bubbles, while passing signals generated by moving bubbles. The relative phase of the multiple data points generated in the clutter filter 500 are then evaluated to generate a velocity estimate according to well-known color-flow processing techniques. As illustrated in step 914 of the method for contrast-agent enhanced color-flow imaging 900, the color-flow processing may include generating a color-encoded display of contrast-agent velocities. It will be appreciated that the color-encoded display may be rendered along with data generated in a B-mode processor to enable identification of the tissue structures imaged. As illustrated in step 916, herein labeled "END," the method for contrast-agent enhanced color-flow imaging 900 may terminate.

It will be appreciated that steps 906 through 914 may be repeated as desired to diagnose various blood vessels of various sizes within the patient. It will be further appreciated that if desired, step 904 may be repeated or continuously performed by introducing the one or more contrast agents via an intravenous line and commercially available infusers. Furthermore, imaging of the one or more contrast agents can comprise simply imaging the concentration of the contrast agents within human tissue, or can comprise color-flow processing as described above to identify the direction and velocity of flow of contrast agents within the bloodstream or tissues.

The techniques described herein compensate for the response of non-moving contrast-agent bubbles, as well as, non-moving tissue. These adjustments are beneficial in that it is now possible to differentiate slowly moving blood flows from surrounding tissue. It will be appreciated that the velocity of contrast agent in the blood is of particular clinical significance, especially when imaging structures such as the heart. As described above, the effects of moving tissue can be substantial, especially when areas near or within the heart are being imaged. Notably, patient breathing, coughing, or other such movements can also create tissue movement. Regardless of the source of the movement, however, it is preferable that this movement is reduced, or compensated for, such that those flash artifacts that degrade the imaging of the contrast agents are suppressed.

It is significant to note that the method for contrast-agent enhanced color-flow imaging 900 is suited to any insonification technique, which suppresses tissue-signal responses at the fundamental frequency of a significant magnitude so that non-linear responses from a contrast image can be detected and color-flow processed to identify direction and velocity.

Figure 10:
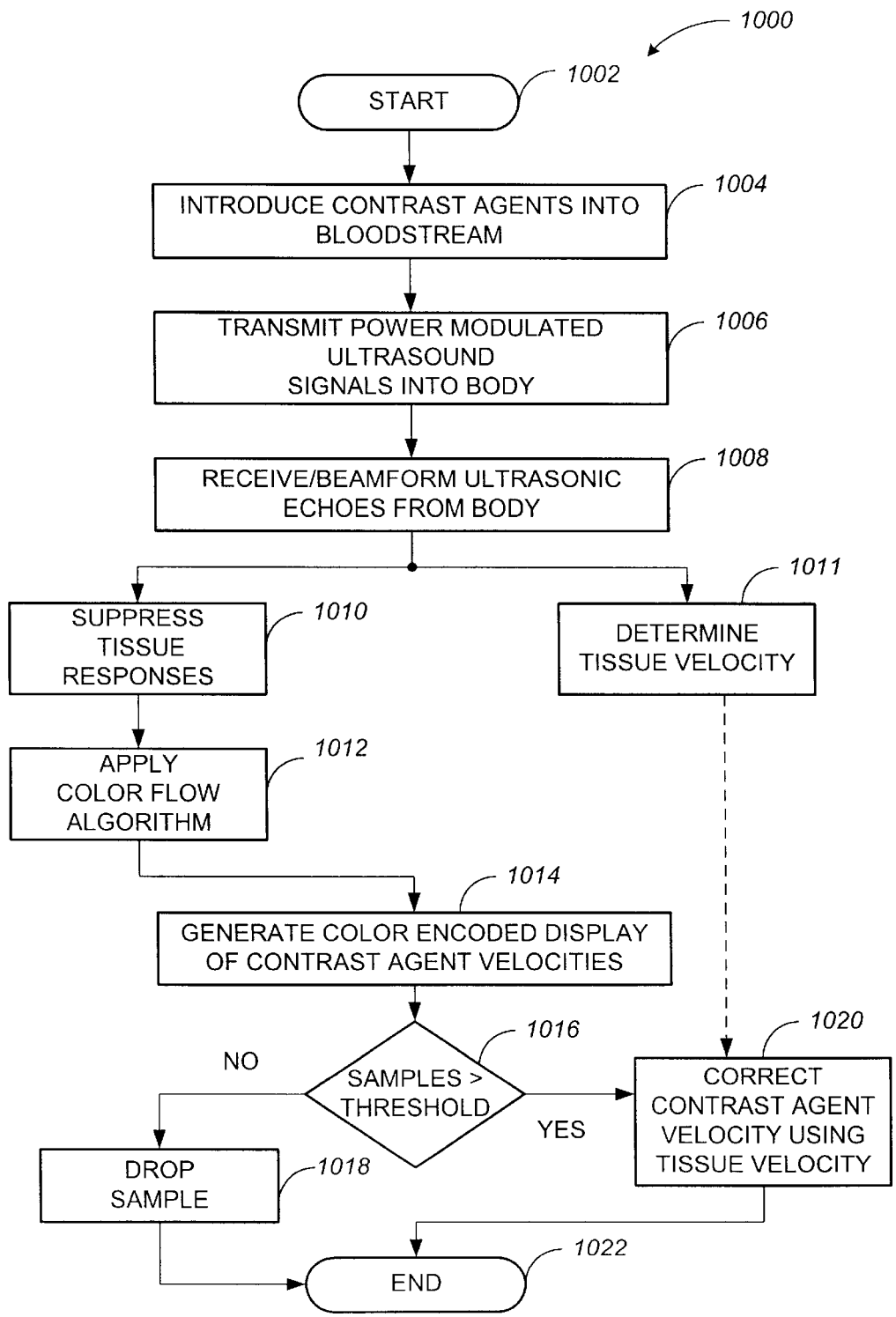
FIG. 10 is a flowchart illustrating a method for generating an improved diagnostic imaging display that reduces the effect of tissue movement to correct blood flow velocity assessments that may be practiced by the ultrasound-imaging system of FIG. 2.

The method for contrast-agent enhanced color-flow imaging 900 having been described with regard to the flow chart of FIG. 9, reference is now directed FIG. 10, which presents a flow chart highlighting a method for contrast-agent enhanced color-flow imaging with a tissue-velocity adjustment. As compared to the method for contrast-agent enhanced color-flow imaging presented in FIG. 9, the method for contrast-agent enhanced color-flow imaging with correction for tissue velocity 1000 presented in FIG. 10 reflects the same steps of "start" 1002, introducing one or more contrast agents 1004, transmitting a series of power modulated ultrasound pulses 1006, and receiving/processing the ultrasound echoes received from the body. Thereafter, and as illustrated in FIG. 10, the method for contrast-agent enhanced color-flow imaging with correction for tissue velocity 1000 branches. A first branch is formed by steps 1010, 1012, and 1014. A second branch is formed by steps 1011 and step 1020, where the first and second processing branches combine.

Within the first processing branch, illustrated in the flow chart of FIG. 10, a power-modulation technique is used to suppress non-linear tissue responses as illustrated in step 1010. After the tissue signals have been suppressed, the various contrast-agent induced echo signals can be processed using a color-flow-processing algorithm as shown in step 1012. The color-flow-processing may include processing by the clutter filter 500 as described hereinabove. As illustrated in step 1014 of the method for contrast-agent enhanced color-flow imaging with correction for tissue velocity 1000, processing may also include generating a color-encoded display of contrast-agent velocities.

Within the second processing branch, a tissue-signal motion processor and a related clutter filter with its own set of coefficients may be used to determine a tissue velocity as shown in step 1011. As illustrated in the flowchart, the tissue velocity determined in step 1011 may be buffered for use later in step 1020 as described below.

Next, as shown in step 1016, the method for contrast-agent enhanced color-flow imaging with correction for tissue velocity 1000 may be configured to compare the contrast-agent color-flow processed velocities with a threshold value. If the velocity samples exceed the threshold, processing may continue with step 1020, where the contrast-agent velocity value is corrected by subtracting the tissue velocity determined in step 1011. Otherwise, if the velocity samples fail to exceed the threshold value, the method for contrast-agent enhanced color-flow imaging with correction for tissue velocity may drop the color-flow processed sample as indicated in step 1018. It will be appreciated that the color-encoded display may be rendered along with data generated in a B-mode processor to enable identification of the tissue structures imaged. As illustrated in step 1022, herein labeled "END," the method for contrast-agent enhanced color-flow imaging with correction for tissue velocity 1000 may terminate. It will be appreciated that steps 1006 through 1020 may be repeated as desired to diagnose various blood vessels of various sizes within the patient. It will be further appreciated that if desired, step 1004 may be repeated or continuously performed by introducing the one or more contrast agents via an intravenous line as previously described.

The techniques described herein compensate for the response of non-moving contrast-agent bubbles, as well as, moving and non-moving tissue generated echoes. These adjustments are beneficial in that it is now possible to differentiate slowly moving blood flows from surrounding tissue while compensating for local tissue movement. Significantly, quantitative assessment of blood flow velocities relative to the surrounding tissue, rather than relative to the transducer 18 face are possible.

It will be appreciated by those having ordinary skill in the art, the improved color-flow processors 400, 800 described above can be implemented in software, hardware, or a combination thereof within the ultrasound-electronics system 1 shown in FIGS. 1 and 2. When implemented in software, the improved color-flow processors 400, 800 can be stored and transported on any computer-readable medium for use by or in connection with an instruction-execution system, apparatus, or device, such as a computer-based system, processor-containing system, or other system that can fetch the instructions from the instruction-execution system, apparatus, or device and execute the instructions.

In the context of this disclosure, a "computer-readable medium" can be any means that can contain, store, communicate, propagate, or transport the program for use by or in connection with the instruction-execution system, apparatus, or device. The computer-readable medium can be, for example, an electronic, magnetic, optical, electromagnetic, infrared, or semiconductor system, apparatus, device, or propagation medium. More specific examples of computer-readable media include the following: an electrical connection having one or more wires, computer diskette, random-access memory (RAM), read-only memory (ROM), erasable-programmable read-only memory (EPROM or Flash memory), an optical fiber, and a compact-disk read-only memory (CD ROM). It is to be noted that the computer-readable medium can even be paper or other suitable media upon which the program is printed as the program can be electronically captured, via for instance optical scanning of the paper or other media, then compiled, interpreted, or otherwise processed and stored in a computer memory.

When implemented in hardware, the improved color-flow processors 400, 800 can be implemented with any or a combination of the following technologies, which are all well known in the art: a discrete-logic circuit(s) having logic gates for implementing logic functions upon data signals, an application-specific integrated circuit (ASIC) having appropriate combinational logic gates, a programmable-gate array(s) (PGA), a field-programmable gate array (FPGA), etc.

It should be emphasized that the above-described embodiments of the present invention are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A method for imaging contrast agents, comprising:
transmitting power-modulated ultrasonic pulses comprising a predetermined transmit sequence having a plurality of transmit lines into a patient's body;
receiving a plurality of ultrasonic echoes comprising contrast-agent generated echoes and tissue-generated echoes from the patient's body;
processing the received ultrasonic echoes to generate a plurality of ultrasonic-echo signals responsive to both the contrast-agent generated and tissue-generated echoes;
processing the plurality of ultrasonic-echo signals to suppress tissue-generated echoes;
processing the plurality of ultrasonic-echo signals to suppress stationary contrast-agent generated echoes;

applying the plurality of contrast-agent generated echo signals to a color-flow algorithm to generate a plurality of data points responsive to contrast-agent motion; and displaying the plurality of data points over time.

2. The method of claim 1, wherein processing to suppress tissue generated signals comprises applying a finite-impulse-response (FIR) filter to the received ultrasonic echoes.

3. The method of claim 1, wherein processing to suppress stationary contrast-agent generated echoes comprises applying a two-stage clutter filter to the received ultrasonic echoes.

4. The method of claim 1, wherein the plurality of data points responsive to contrast-agent motion contain information related to direction of motion and relative velocity.

5. The method of claim 1, wherein the plurality of transmit lines are generated with transmit signals having different voltage amplitudes.

6. The method of claim 1, wherein the plurality of transmit lines are generated with transmit signals having different phases.

7. The method of claim 1, wherein the plurality of transmit lines are generated with transmit signals having different polarities.

8. The method of claim 1, wherein the plurality of data points responsive to contrast-agent motion contain information related to direction of motion and relative velocity.

9. The method of claim 2, wherein a plurality of first coefficients are applied to the received ultrasonic echoes.

10. The method of claim 4, wherein displaying is performed after a determination that the intensity of the velocity information exceeds a threshold.

11. The method of claim 4, wherein displaying is performed after correcting the velocity information for tissue motion.

12. The method of claim 9, wherein a plurality of second coefficients are applied to the received ultrasonic echoes.

13. The method of claim 10, wherein B-mode image data is displayed after a determination that the intensity of the velocity information fails to meet the threshold.

14. An improved ultrasound-imaging system, comprising:

an excitation-signal source configured to generate a power-modulated transmit-line sequence;

a transducer coupled to the excitation-signal source, the transducer configured to emit a plurality of ultrasonic-pulses responsive to the power-modulated transmit-line sequence into a medium and to convert a plurality of received ultrasonic echoes responsive to both tissue and one or more contrast agents within the medium to a plurality of echo signals;

an ultrasound-processing system coupled to the transducer, the ultrasound-processing system configured to reduce tissue-generated ultrasonic-echo signals and reduce stationary contrast-agent generated ultrasonic-echo signals, while passing ultrasonic-echo signals generated from moving contrast agent; and a display-processing system coupled to the ultrasound-processing system, the display-processing system configured to receive and generate a graphic representation responsive to the ultrasonic-echo signals generated from moving contrast agent.

15. The system of claim 14, wherein the power-modulated transmit-line sequence is generated with transmit signals having different voltage amplitudes.

16. The system of claim 14, wherein the power-modulated transmit-line sequence is generated with transmit signals having different polarities.

17. The system of claim 14, wherein the power-modulated transmit-line sequence is generated with transmit signals having different phases.

18. The system of claim 14, wherein the ultrasound-processing system comprises a clutter filter.

19. The system of claim 18, wherein the ultrasound-processing system comprises a plurality of two-dimensional imaging processors.

20. The system of claim 19, wherein the ultrasound-processing system comprises a color-flow processor.

21. The system of claim 18, wherein the clutter filter comprises a multiple sample one-zero filter.

22. The system of claim 21, wherein the clutter filter time shifts the zero between adjacent ultrasonic-echo signal samples.

23. The system of claim 22, further comprising:

a tissue-velocity processor coupled to the ultrasound-processing system, the tissue-velocity processor configured to generate a first output signal responsive to motion of tissue-generated ultrasonic-echo signals;

an arbiter coupled to a second output signal from the color-flow processor and a third output signal from at least one of the plurality of two-dimensional image processors, the arbiter configured to forward the second output signal from the color-flow processor when the intensity of the second output signal exceeds a threshold; and an arithmetic junction coupled to an output of the arbiter and the first output signal, the arithmetic junction configured to perform a subtraction of the first output signal from the second output signal.

24. The system of claim 23, wherein the arbiter is configured to forward the third output signal from at least one of the plurality of two-dimensional image processors when the intensity of the second output signal fails to exceed a threshold.

* * * * *